(12) United States Patent
Hintermann et al.

(10) Patent No.: US 11,547,456 B2
(45) Date of Patent: Jan. 10, 2023

(54) INTERNAL ANKLE FIXATION SYSTEMS, FOOT SECUREMENT AND JIG DEVICES, AND RELATED METHODS

(71) Applicant: DT MEDTECH, LLC, Baltimore, MD (US)

(72) Inventors: Beat Hintermann, Liestal (CH); Shawn Huxel, Seaside Park, NJ (US)

(73) Assignee: DT Medtech, LLC, McMinnville, TN (US)

( * ) Notice: Subject to any disclaimer, the term of this patent is extended or adjusted under 35 U.S.C. 154(b) by 0 days.

(21) Appl. No.: 16/477,759

(22) PCT Filed: Jan. 12, 2018

(86) PCT No.: PCT/US2018/013658
§ 371 (c)(1),
(2) Date: Jul. 12, 2019

(87) PCT Pub. No.: WO2018/132764
PCT Pub. Date: Jul. 19, 2018

(65) Prior Publication Data
US 2019/0365435 A1 Dec. 5, 2019

Related U.S. Application Data

(60) Provisional application No. 62/445,464, filed on Jan. 12, 2017.

(51) Int. Cl.
*A61B 17/72* (2006.01)
*A61B 17/88* (2006.01)
(Continued)

(52) U.S. Cl.
CPC ........ *A61B 17/7291* (2013.01); *A61B 17/725* (2013.01); *A61B 17/7241* (2013.01);
(Continued)

(58) Field of Classification Search
CPC ............ A61B 17/7291; A61B 17/7241; A61B 17/725; A61B 17/7283; A61B 17/8685
(Continued)

(56) References Cited

U.S. PATENT DOCUMENTS 6,579,293 B1 6/2003 Chandran
6,719,759 B2 * 4/2004 Wagner .............. A61B 17/8057
606/280

(Continued)

FOREIGN PATENT DOCUMENTS

EP 0715832 A2 * 6/1996 ......... A61B 17/1721
EP 3485831 A1 * 5/2019 ........... A61B 17/744
(Continued)

OTHER PUBLICATIONS

Thomas, S., International Search Report and Written Opinion of the International Searching Authority for PCT/US2018/013658, dated May 4, 2018, pp. 1-19.
(Continued)

*Primary Examiner* — Eduardo C Robert
*Assistant Examiner* — Christina NegrelliRodriguez
(74) *Attorney, Agent, or Firm* — Reed Smith LLP; Matthew P. Frederick; John M. Cogill

(57) ABSTRACT

Embodiments described herein provide an implant for rigid intramedullary fixation of the hindfoot complex with the midfoot and/or forefoot and methods of implanting the same. Embodiments described herein can allow for the implant to be adapted to the patient based upon the extent of bone loss and instability. Embodiments herein also provide a jig system to facilitate the shaping of the foot and/or the implantation of the described internal fixation systems.

18 Claims, 11 Drawing Sheets

(51) Int. Cl.
 *A61B 17/68* (2006.01)
 *A61B 17/90* (2006.01)

(52) U.S. Cl.
 CPC .......... *A61B 17/7283* (2013.01); *A61B 17/88* (2013.01); *A61B 17/90* (2021.08); *A61B 2017/681* (2013.01)

(58) Field of Classification Search
 USPC ........................................................ 606/62
 See application file for complete search history.

(56) References Cited

U.S. PATENT DOCUMENTS

| | | | | |
|---|---|---|---|---|
| 8,562,606 | B2* | 10/2013 | Richter | A61B 17/8897 |
| | | | | 606/64 |
| 10,869,701 | B2* | 12/2020 | Van Dyke | A61B 17/8665 |
| 10,925,650 | B2* | 2/2021 | Simon | A61B 17/7225 |
| 2006/0200141 | A1* | 9/2006 | Janna | A61B 17/7233 |
| | | | | 606/62 |
| 2008/0294164 | A1* | 11/2008 | Frank | A61B 17/7241 |
| | | | | 606/64 |
| 2009/0149861 | A1 | 6/2009 | Brodsky | |
| 2010/0121325 | A1 | 5/2010 | Tyber et al. | |
| 2011/0251614 | A1 | 10/2011 | Piraino | |
| 2011/0282397 | A1 | 11/2011 | Richter et al. | |
| 2012/0053639 | A1 | 3/2012 | Grant | |
| 2012/0330313 | A1* | 12/2012 | Grady | A61B 17/7225 |
| | | | | 606/64 |
| 2015/0012048 | A1 | 1/2015 | Huebner et al. | |
| 2015/0032168 | A1* | 1/2015 | Orsak | A61B 17/1775 |
| | | | | 606/304 |
| 2016/0058484 | A1* | 3/2016 | McCombs-Stearnes | A61B 17/7283 |
| | | | | 606/62 |
| 2016/0089245 | A1* | 3/2016 | Early | A61F 2/4202 |
| | | | | 623/21.18 |
| 2016/0338842 | A1* | 11/2016 | Adams | A61B 17/7291 |
| 2018/0263669 | A1* | 9/2018 | Peterson | A61B 17/863 |

FOREIGN PATENT DOCUMENTS

| | | | | |
|---|---|---|---|---|
| WO | 20090153071 | A2 | 12/2009 | |
| WO | 2014057332 | A1 | 4/2014 | |
| WO | WO-2019024741 | A1 * | 2/2019 | .......... A61B 17/744 |

OTHER PUBLICATIONS

Partial Supplementary European Search Report dated Jun. 22, 2020 for EP Patent Application No. 18738990.3.

* cited by examiner

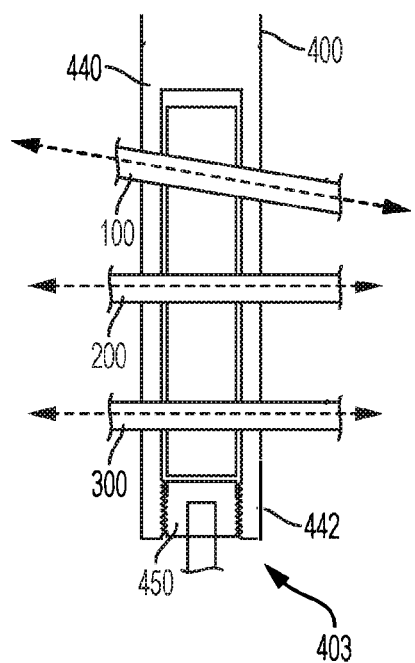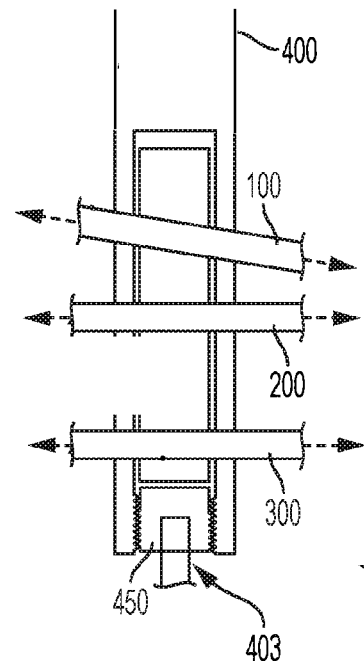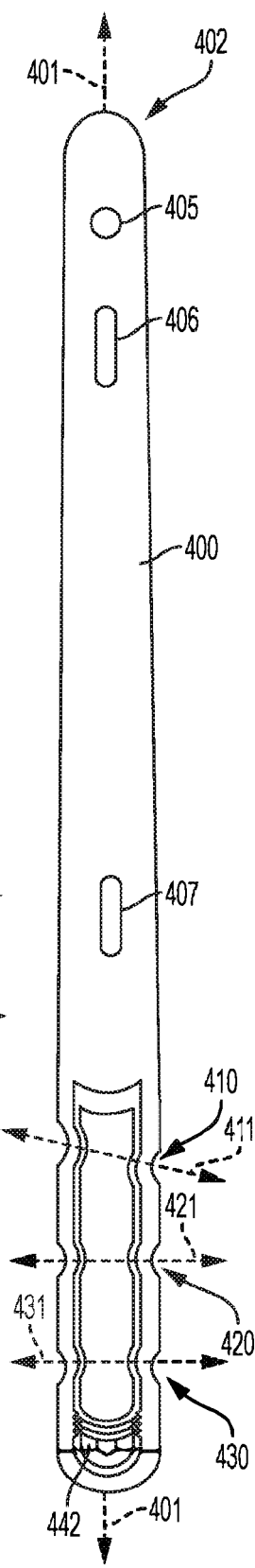
FIG. 2A(i)  FIG. 2A(ii)  FIG. 2B

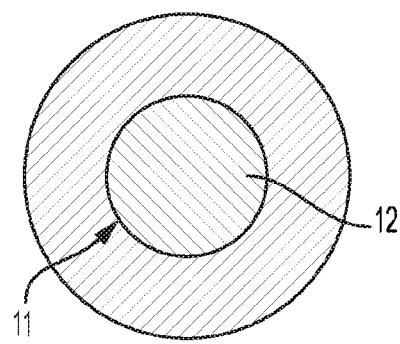
FIG. 3E(i)
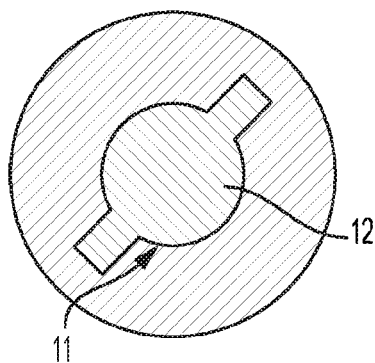
FIG. 3E(ii)
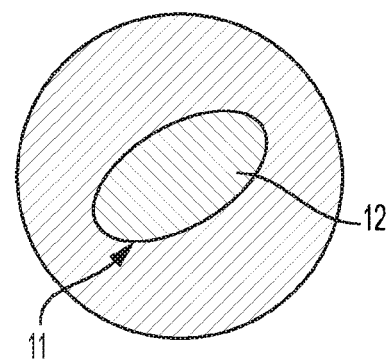
FIG. 3E(iii)

INTERNAL ANKLE FIXATION SYSTEMS, FOOT SECUREMENT AND JIG DEVICES, AND RELATED METHODS

CROSS REFERENCE TO RELATED APPLICATION

This application claims priority to U.S. Provisional Application No. 62/445,464, filed Jan. 12, 2017. The contents of which are incorporated by reference in their entirety.

TECHNICAL FIELD

The present application relates to the technical field of internal joint fixation and stabilization, and more particularly to fastener assemblies and methods that provide stable fixation of the hindfoot.

BACKGROUND

Ankle fusion typically involves using various fasteners (e.g., nails, pins, screws, etc.) to hold the bones together. In a typical fusion surgery, the ankle joint is fused, allowing the tibia (shinbone) to grow together or fuse with the talus bone, the bone of the ankle that would normally articulate with the tibia and fibula, and the calcaneus, the bone that forms the ankle joint. A long ankle arthrodesis "nail" may be inserted through the heel and fixed into place with screws or pins. Often, one or more screws or pins are inserted into the calcaneus, the bone at the lower back part of the foot forming the heel, which provides more stability.

This type of surgical correction and fixation can be required in instances of complex deformities and instabilities of the foot and ankle that are associated with loss of bone stock (e.g. after extended injuries, failed primary reconstruction, failed ankle prostheses), neuropathic bone disruption (e.g. Charcot neuroarthropathy), neurogenic disorders (e.g. irreducible muscular contractures, not managing deformation forces, not manageable muscular palsy), and soft tissue deficiencies (e.g. loss of soft tissues, unstable scars). For such conditions, one goal of treatment is to obtain a stable foot in neutral position that allows the patient to fully weight-bear his or her foot without fear of further damage to the plantar skin (e.g. avoidance of ulceration).

Achieving such a goal with internal fixation is challenging because current devices do not provide adequate support in a transverse/axial plane (e.g., in the midfoot or forefoot region), nor in the sagittal and coronal plane (e.g., in the hindfoot or ankle region). In particular, plate and screw fixation often fail because of inadequate bone healing, loss of fixation, or fatigue. Alternatively, intramedullary fixation that utilizes a tibial rod, may withstand some of the forces, but these solutions fail to achieve stability in the midfoot and forefoot.

For this reason, many clinicians continue to use an external fixator. However, this treatment modality is time consuming for the surgeon and the surrounding paramedical staff and is often associated with additional problems, such as pin tract infections. Patients do not generally like this treatment because of long-time impairment and the very demanding daily care.

Another issue with complex reconstructions or stabilizations of the foot and ankle encountered by surgeons is the ability to obtain a foot in neutral position in all three planes and to restore the longitudinal arch 52 to avoid or relieve pain and ulceration beneath the midfoot. Part of the difficulty derives from being unable to observe the foot in a loaded condition.

SUMMARY

Embodiments described herein provide an implant for rigid intramedullary fixation of the hindfoot complex with the midfoot and/or forefoot. Embodiments described herein can allow for the implant to be adapted to the patient based upon the extent of bone loss and instability. If the ankle joint is involved in the disorder, a long fastener can be used for tibiocalcaneal fixation. If the ankle joint is intact and not included in the disorder, a short fastener in the hindfoot preserving the ankle joint can be used for rigid internal fixation of a part or the whole foot.

Embodiments described herein provide a foot securement and jig device that can approximate the shape of the foot under the load of walking. Embodiments described herein provide a foot securement and jig device that adjusts and/or maintains the shape of the longitudinal arch of the foot. Embodiments described herein provide a foot securement and jig device that is configured to adjust the position of the foot relative to the tibia and to firmly fix the foot's position relative to the jig. Embodiments described herein provide a foot securement and jig device that allows for a visual or non-radiographic alignment of the foot relative to the jig device. Once the desired foot position is obtained, compression forces can be applied, and a series of fasteners can be inserted potentially without the use of a guiding wire.

Other embodiments described herein provide a method of implanting an internal fixation ankle support system into a patient comprising inserting a first elongated member into a calcaneus and talus or calcaneus, talus, and tibia of the patient and inserting a second elongated member into the talus and at least one of a cuboid, a cuneiform, or a first metatarsal of the patient, wherein the second elongated member intersects with the first elongated member.

Other embodiments described herein provide a method of shaping a deformed foot prior to implanting an ankle fixation device. The method comprises securing a foot to jig system and applying pressure to the foot with upper and lower presses or clamps mounted to the jig system as described herein.

These and other aspects, objects, features and embodiments will be apparent from the following description and the appended claims. Those skilled in the art may use the components of the ankle prosthesis together or separate and may apply techniques provided herein for other applications. In describing the aspects and objects of the ankle prosthesis, the use of first, second, third, and so on are used for the purposes of clarity and are not intended to modify a term to which it is associated and should not be construed to add any further limitation.

BRIEF DESCRIPTION OF THE DRAWINGS

The drawings illustrate only example embodiments of an internal ankle fixation and stabilization system and of a foot securement and jig device and are therefore not to be considered limiting of its scope.

FIG. 2A(i) illustrates a partial, cross-sectional view of the embodiment shown in FIG. 1A where element 400 is in an unlocked state.

FIG. 2A(ii) illustrates a partial, cross-sectional view of the embodiment shown in FIG. 1A where element 400 is in a locked state.

FIG. 2B illustrates a schematic, cross-sectional view of element 400 shown in FIG. 1A.

FIGS. 3E(i) to 3E(iii) illustrates a schematic of a cross-section of an elongated fastener.

DETAILED DESCRIPTION OF EXAMPLE EMBODIMENTS

Figure 1A:
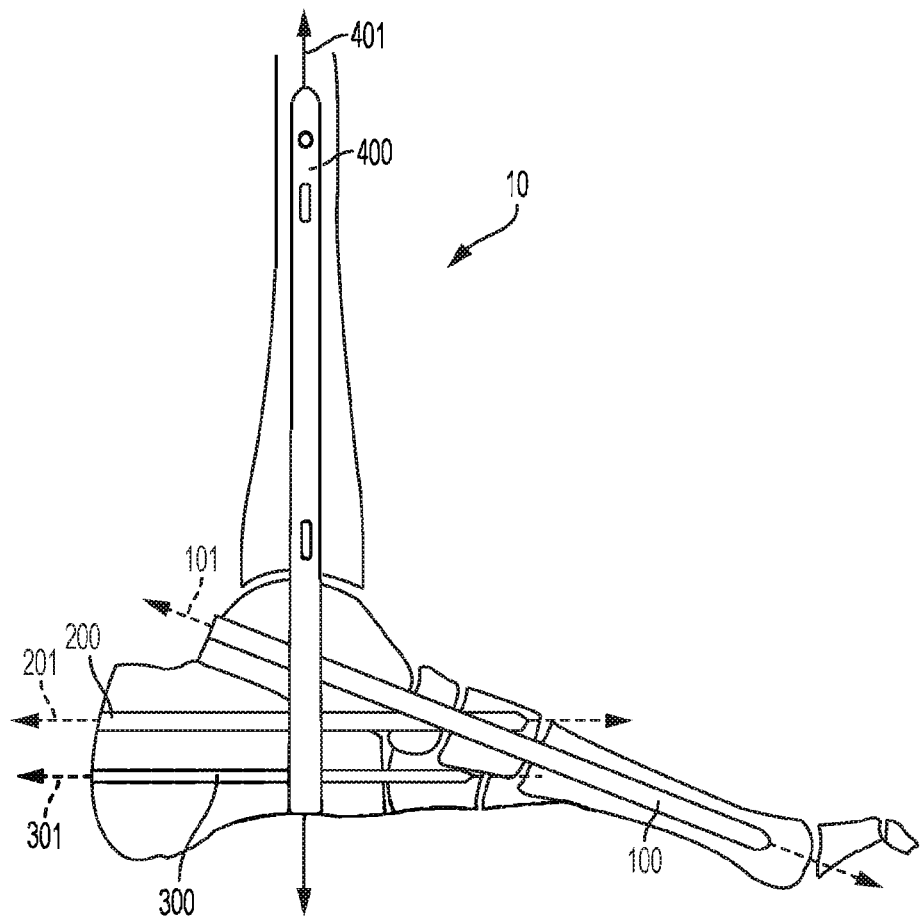
FIG. 1A illustrates a side schematic view of an embodiment of an internal ankle fixation system implanted in the foot and tibia in accordance with the present disclosure.
Figure 1B:
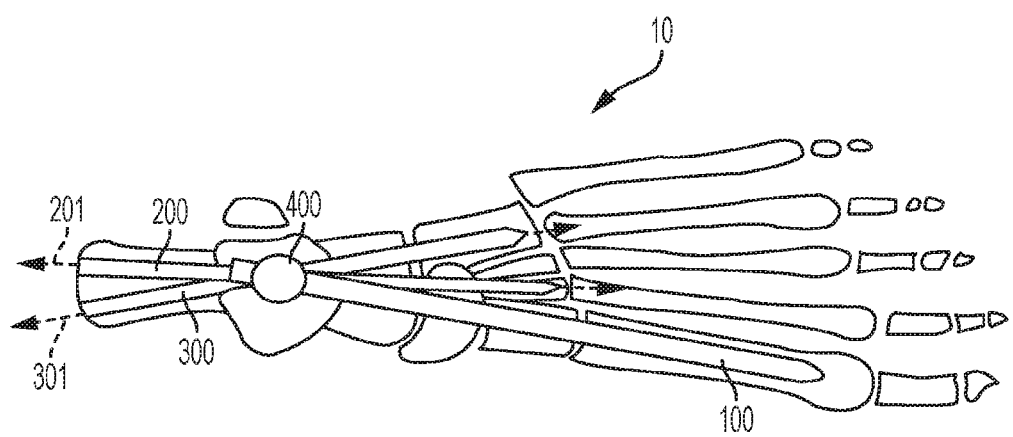
FIG. 1B illustrates a top schematic view of the embodiment shown in FIG. 1A.

An embodiment of an internal ankle fixation system according to the invention is illustrated in FIGS. 1A and 1B. Internal ankle fixation system 10 includes a first elongated fastener 100 having a first longitudinal axis 101, a second elongated fastener 200 having a second longitudinal axis 201, an third elongated fastener 300 having a third longitudinal axis 301, and a fourth elongated fastener 400. A more detailed schematic view of the fourth elongated fastener 400 is illustrated in FIGS. 2A(i), 2A(ii) and 2B. An elongated fastener is configured to be inserted into or through bone. Examples of elongated fasteners include intramedullary bone nails, screws, pins and the like.

Fourth elongated fastener 400 has a longitudinal axis 401 extending between a first end 402 and a second end 403 of the fourth elongated fastener and is configured to intersect with the first, second and third elongated fasteners 100, 200, 300. Fourth elongated fastener 400 comprises a first hole 410 configured to receive the first elongated fastener 100 along a first axis 411, a second hole 420 configured to receive the second elongated fastener 200 along a second axis 421, and a third hole 430 configured to receive the third elongated fastener 300 along a third axis 431. Second hole 420 and third hole 430 are located between the second end 403 of fourth elongated fastener 400 and first hole 410. Each of elongated fasteners 100, 200, 300 when extending through a respective hole 410, 420, 430 is intersecting fourth elongated fastener 400.

Fourth elongated fastener 400 can be configured to be initially inserted into a calcaneus bone and into the talus bone. First end 402 of fourth elongated fastener 400 is more tapered and/or has a smaller transverse dimension than the second end 403, as the first end 402 is the end that will be first inserted. In the embodiment shown, fourth elongated fastener 400 is an intramedullary nail.

Internal ankle fixation system 10 is configured to provide fixation of the midfoot or the midfoot and forefoot coupled to fixation of the hindfoot. In particular, first, second, and third elongated fasteners 100, 200, 300 are configured to have the size (length and dimension) and shape that facilitates insertion into a particular foot bone for purposes of fixation relative to the talus bone. For example, in some embodiments, first elongated fastener 100 has a length that is sufficient to extend between and into a talus and a first metatarsal of a patient when implanted. In addition, first hole 410 is configured such that first axis 411 would intersect with the first metatarsal when fourth elongated fastener 400 is implanted in a patient. In some embodiments, second elongated fastener 200 has a length that is sufficient to extend between and into a calcaneus and a second cuneiform of a patient when implanted, and second hole 420 is configured such that second axis 421 would intersect with the second cuneiform when fourth elongated fastener 400 is implanted in a patient. In some embodiments, third elongated fastener 300 has a length that is sufficient to extend between and into a calcaneus and a cuboid of a patient when implanted, and third hole 430 is configured such that third axis 431 would intersect with the cuboid when fourth elongated fastener 400 is implanted in a patient.

To accommodate the differences in the sizes of bones in the hindfoot relative to the midfoot or forefoot, the first, second; and third elongated fasteners 100, 200, 300 can be tapered along the length or a portion thereof, the smaller outer diameter section being intended for the midfoot or the forefoot.

Moreover, in some embodiments, first elongated fastener 100 can be longer than the second and third elongated fasteners 200, 300. First elongated fastener 100 can be at least 130%, 140%, 150%, 160%, 170%, 180%, 190%, 200%, 210% or 220% the length of the second and/or third elongated fastener 200, 300. Second elongated fastener 200 can be longer than the third elongated fastener 300, such as at least 105%, 108%, 110%, 113%, 115%, 118%, 120%, 123%, 125% or 130% longer.

In some embodiments, fourth elongated fastener 400 has a transverse dimension that is greater than that of each of the other elongated fasteners 100, 200, 300 such that the other elongated fasteners can pass through or intersect with the fourth elongated fastener 400. In some embodiments, a transverse dimension of the first elongated fastener 100 is greater than a transverse dimension of the second elongated fastener 200. In some embodiments, a transverse dimension of the first elongated fastener 100 is greater than a transverse dimension of the third elongated fastener 300.

In some embodiments, first axis 411 and the longitudinal axis 401 of the fourth elongated fastener 400 are oblique. In some embodiments, second axis 421 and the longitudinal axis 401 of the fourth elongated fastener 400 are perpendicular. In some embodiments, third axis 431 and the longitudinal axis 401 of the fourth elongated fastener 400 are perpendicular. In some embodiments, second axis 421 and the third axis 431 are skew. In some embodiments, first axis 411 and the second axis 421 are skew. In some embodiments, first axis and the third axis are skew.

Ankle fixation system 10 can be configured such that movement (e.g., axial, angular, lateral and/or torsional movement) of the first, second and/or third elongated fastener 100, 200, 300 relative to fourth elongated fastener 400 is impeded or prevented. For example, FIGS. 2A(i) and (ii) illustrates a cross-sectional, schematic of a section of the fourth elongate fastener 400, at the second end. As illustrated, in some embodiments, fourth elongate fastener 400 can be configured to change the transverse, cross-sectional shape or area (transverse being perpendicular to axis) of the holes 410, 420, 430 through which the other fasteners extend, thereby frictionally binding the other elongate fasteners 100, 200, 300 when extended through such holes. Fourth elongate fastener 400 can comprise a longitudinal bore 440 comprising an internal thread 442 and being accessible at the second end 403 and a compression screw 450 configured to be inserted into longitudinal bore 440. Both the section comprising longitudinal bore 440 and compression screw 450 each have a plurality of holes that form first, second and third holes 410, 420, 430 when aligned. When system 10 is assembled, rotating compression screw 450 (via access at second end 403 of fourth elongate fastener 400) can move first, second and third elongate fasteners 100, 200, 300 in the direction of the longitudinal axis 401 of the fourth elongate fastener 400, thereby causing the aligned holes of the longitudinal bore 440 and compression screw 450 to become misaligned and frictionally binding first, second, and third elongate fastener 100, 200, 300.

First, second, third and/or fourth elongated fasteners 100, 200, 300, 400 comprises one or more pure or alloyed metals selected from a group consisting of stainless steel, cobalt, chromium, titanium and tantalum.

Fourth elongated fastener 400, as shown in FIGS. 1A and 1B and FIGS. 2A(i), A(ii) and 2B, can have a length that is sufficient to extend between and into a calcaneus and a tibia, passing through a talus of a patient when implanted. To facilitate securing fourth elongated fastener 400 to the tibia, fourth elongated fastener 400 can comprise one or more holes or slots configured such that another fastener (e.g., pin, nail or screw) can pass therethrough. For example, with reference to FIG. 2B, fourth elongated fastener 400 comprises a fourth hole 405 that is located between the first end and the first hole 410. In some embodiments, fourth elongated fastener comprises a first slot 406 that is located between the fourth hole 405 and the first hole 410. In addition, in some embodiments, fourth elongated fastener 400 can comprise a second slot 407 that is located between the first slot 406 and the first hole 410.

In some embodiments, ankle fixation system 10 can be configured for polyaxial coupling of the first, second and/or third elongated fastener 100, 200, 300 to the fourth elongated fastener 400, whereby a single fixation system 10 is compatible with a wide range of foot anatomies. More specifically, the first, second and/or third holes 410, 420, 430 of the fourth elongated fastener 400 and the first, second and/or third elongated fastener 100, 200, 300 can be configured in the manner shown in FIG. 3A.

Figure 3A:
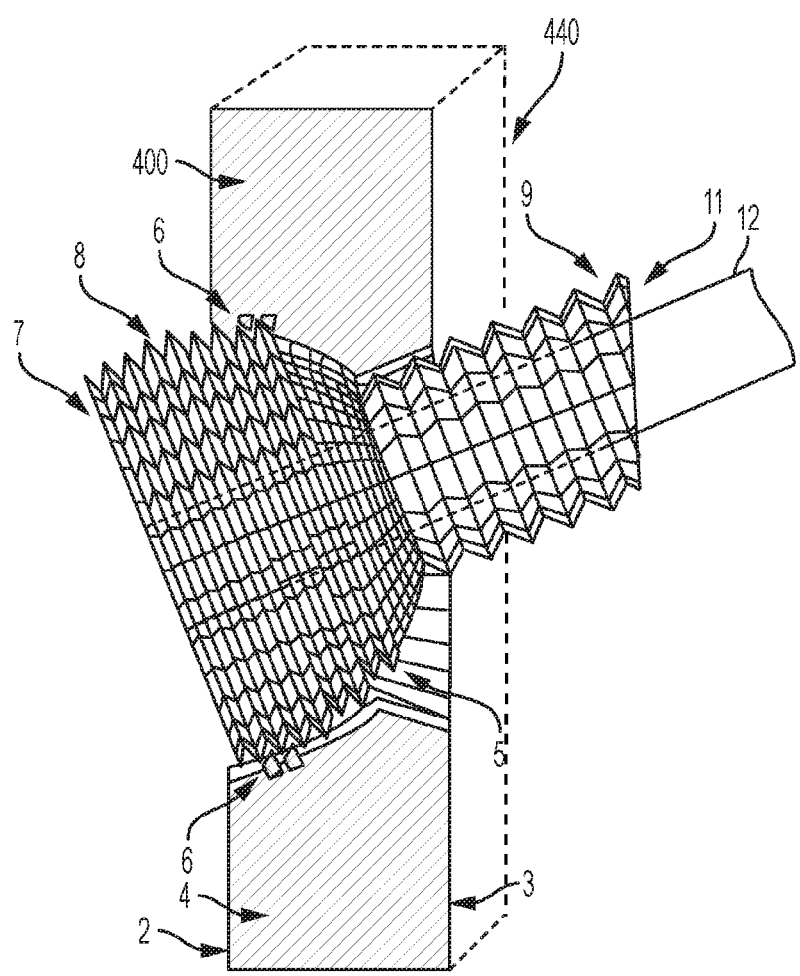
FIG. 3A illustrates a schematic of a variable angle coupling between two intersecting elongated fasteners.
Figure 3B:
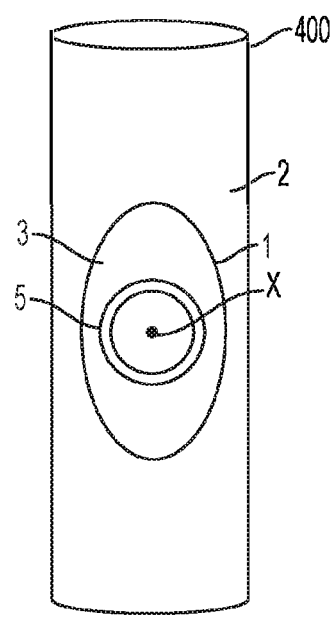
FIG. 3B illustrates a schematic of an opening in the intersected elongated fastener.

FIG. 3A shows a cross-sectional view of an outer surface 2 and an inner surface 3 of wall 4, wherein the inner surface is defining a longitudinal bore 440 of the fourth elongate member 400 (see FIGS. 2A and 2B.). FIG. 3A further shows a hole 5 (e.g., holes 410, 420, 430) in the wall 4 configured to receive a bone screw 7 (e.g., a first, second and/or third elongated fastener 100, 200, 300) and couple in fixed relation thereto at a variety of angles. In the embodiment shown, hole 5 defined by the wall 4 of the fourth elongated member 400 can have an hourglass shape. The hourglass shape can comprise two partial spheres merged into one another or two frustoconical shapes merged to one another. In the wall 4 opposite the hole 5 with an hourglass shape (or the posterior hole 5) will be an elongated or oval-shaped hole 1 (or anterior hole 1) as shown in FIG. 3B. The shapes of posterior hole 5 and anterior hole 1 facilitate the axial adjustment of the screw 7.

The screw 7 has a head 8 and a shank 9. The head 8 is shaped like a partial sphere and is threaded, e.g., helical grooves on the under surface of the head. In some embodiments, the threading can have a pitch that is different than the pitch of the threaded shank 9, if the shank 9 is also threaded. With such a configuration, the screw 7 can be introduced in alignment with the axis X (FIG. 3B, projecting out of the page), which is defined by a line extending between the centers of posterior hole 5 and anterior hole 1, and locked relative to the fourth elongated member 400. However, the configuration shown in FIG. 3A also allows for the screw to be introduced off-axis from the axis X and locked relative to the fourth elongated member 400. The degree to which the screw can be off-axis from axis X can vary according with the design. In the embodiment shown, up to 20 degrees of angulation in any direction may be allowed.

In order to lock, in the embodiment shown, the surface defining each hole 5 can have, for example, a small number of isolated protrusions 6 (such as pegs or spikes), which number is within 2 and 30, designed to lock against the threaded spherical head 8 of the screw 7 when the screw is driven through the hole 5. Once the screw 7 has been driven in, it locks tightly against the protrusions 6 on the surface defining the hole 5. Alternatively, in a variation on the embodiment shown, the surface defining each hole 5 is smooth, and when driving the screw through the hole, the threads of the spherical head 8 of the screw 7 can gall the surface of the hole 5, thereby locking the screw relative to the fourth elongated fastener 400.

Figure 3C:
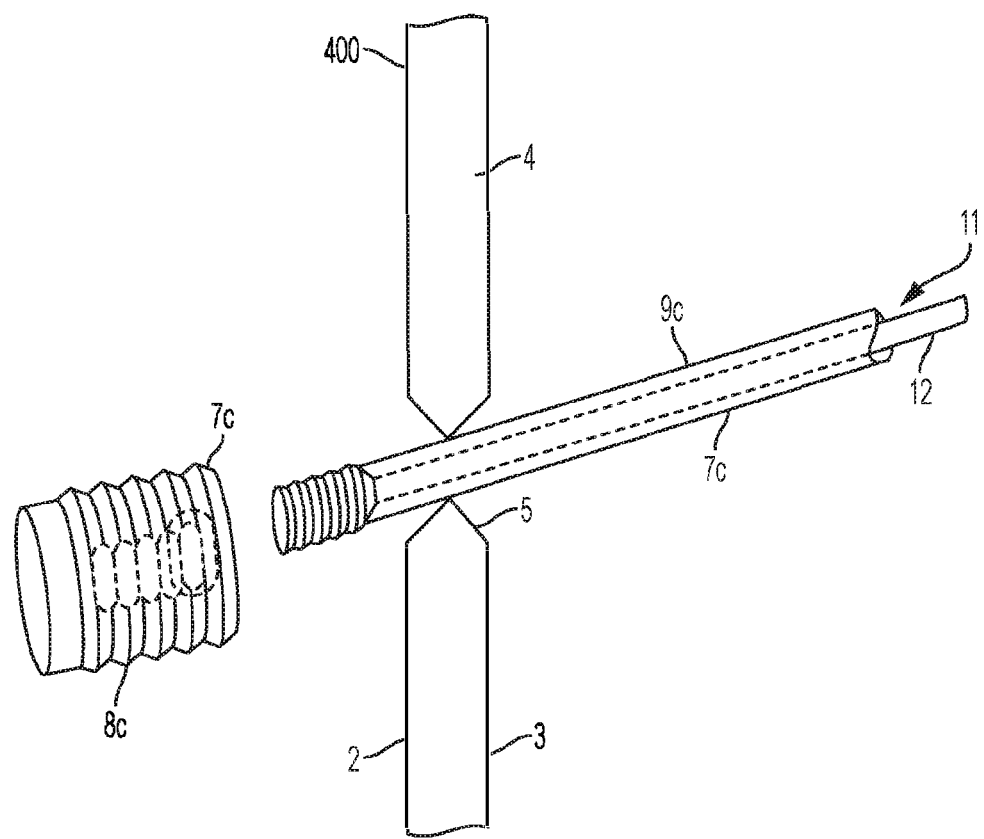
FIG. 3C illustrates a schematic of a variable angle coupling between two intersecting elongated fasteners.

In another embodiment configured for polyaxial coupling, as shown in FIG. 3C, an elongated fastener 7c can comprise head 8c configured to couple and decouple with the shank 9c. Shank 9c has a threaded end that is configured to receive a threaded hole accessible on the underside of head 8c. The underside of head 8c can be threaded like that shown in FIG. 3A to lock against the surface defining hole 5.

Figure 3D:
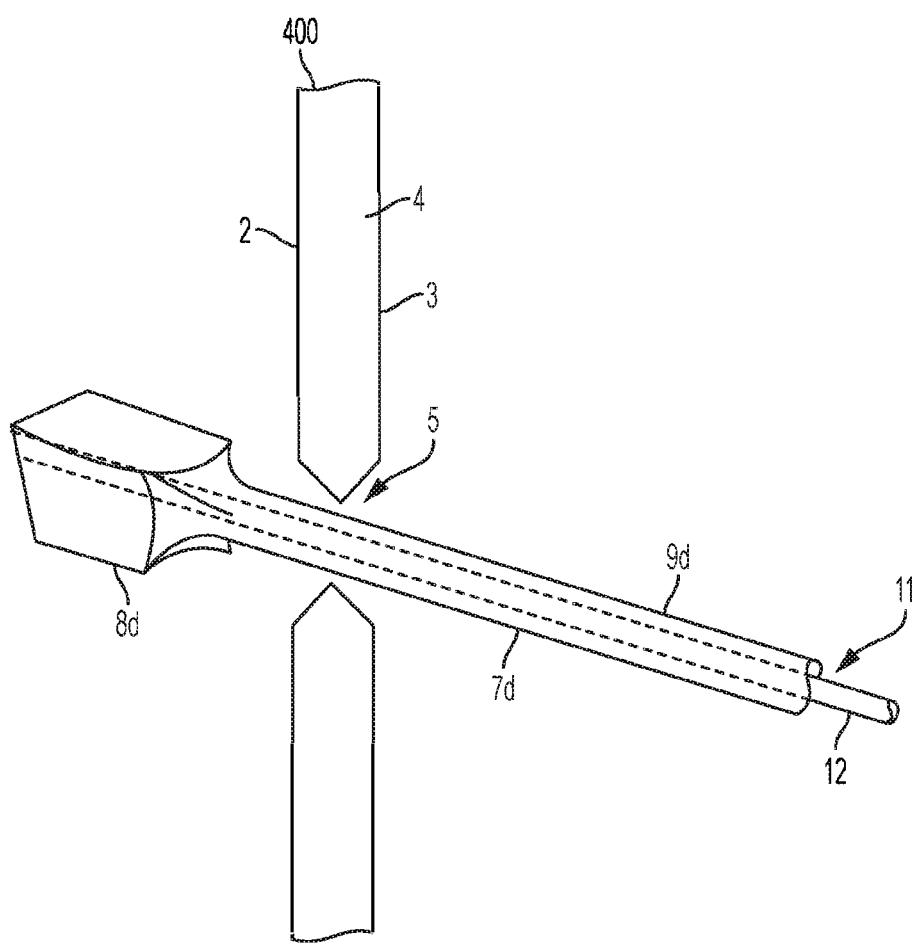
FIG. 3D illustrates a schematic of a variable angle coupling between two intersecting elongated fasteners.

In yet another embodiment configured for polyaxial coupling, as shown in FIG. 3D, an elongated fastener 7 d can comprise a shank 9 d and a head 8 d that is star, rectangular (e.g., square) or triangular shaped, for example, and that is composed of a material that is harder than that of the fourth elongated member. The head 8 d, when driving the fastener 7 d through the hole, will deform against the surface of the hole, thereby locking the screw relative to the fourth elongated fastener 400.

In some embodiments, the first, second and/or third elongated fastener 100, 200, 300 have a solid body. In other embodiments, the first, second and/or third elongated fastener 100, 200, 300 can be configured for insertion over a guide wire and for receiving a reinforcing member, e.g., a stiff rod, once positioned and the wire removed. For example, as shown in FIGS. 3A, 3C and 3D, screw 7 and elongated fasteners 7c, 7d have a longitudinal bore 11 extending the length thereof and configured to receive an elongated reinforcing member 12. Once the screw 7 or elongated fastener 7c or 7d are in position, an elongated reinforcing member 12 can be inserted into the longitudinal bore 11. The elongated reinforcing member 12 is configured to extend at least 80%, 90%, 95%, or 100% of the length of the longitudinal bore 11. The elongated reinforcing member 12 is composed of a material that has a hardness, elastic modulus, or both that is greater than that of the screw 7 or elongated fastener 7c or 7d.

The cross-sectional shape of the reinforcing member 12 and the longitudinal bore 11 of the first, second, or third elongated member can be configured for isotropic or anisotropic deformation and support during use. The cross-sectional shape shown in FIG. 3E(i) allows for isotropic deformation as it is circular for both the reinforcing member 12 and the longitudinal bore 11. In comparison, the cross-sectional shapes shown in FIGS. 3E(ii) and (iii) allows for anisotropic deformation and strength. In FIG. 3E(ii) and (iii), the cross-sectional shapes for both the reinforcing member 12 and the longitudinal bore 11 are oblong (e.g., oval or rectangular).

During insertion of the reinforcing member 12, the fourth elongated member 400 is sufficiently immobilized, either directly or through the jig system, to support the counter-force.

Figure 4:
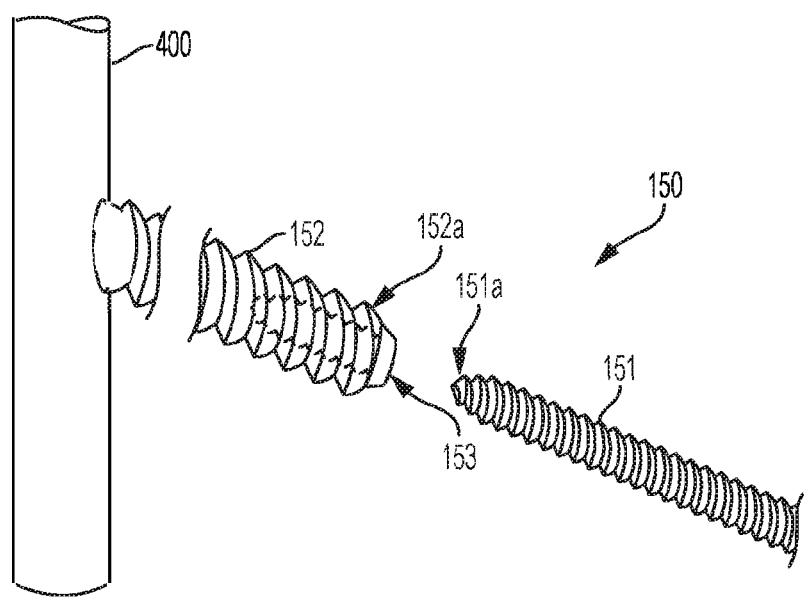
FIG. 4 illustrates a schematic of a two-piece elongated fastener.

In some embodiments, with reference to FIG. 4, the first, second and/or third elongated fastener 100, 200, 300 can be configured to be a two-component elongated fastener 150, wherein a first component 151 is configured to be inserted in an anterior to posterior direction, such as into a first metatarsal, and a second component 152 is configured to be is inserted in a posterior to anterior direction, such as into the talus or the calcaneus and the bones of the midfoot. Each component 151, 152 has an end 151a, 152a that is configured to be inserted into bone, such as a tapered end. The insertable ends 151a, 152a of the two component 151, 152 meet and are coupled to each other at an intermediate point, such as at a point near a deformity, e.g., collapsed midfoot. In the embodiment shown, the two components 151, 152 are configured to threadably couple together at the insertable ends 151a, 152a. The first piece 151, which is inserted in an anterior to posterior direction, has a smaller outer diameter (OD) than the second component 152 and is configured to be inserted into a threaded bore 153 at the tapered end 152a of the second component 152. The cross section of each component is sufficient to meet the load requirements of the respective regions of the foot.

Figure 5A:
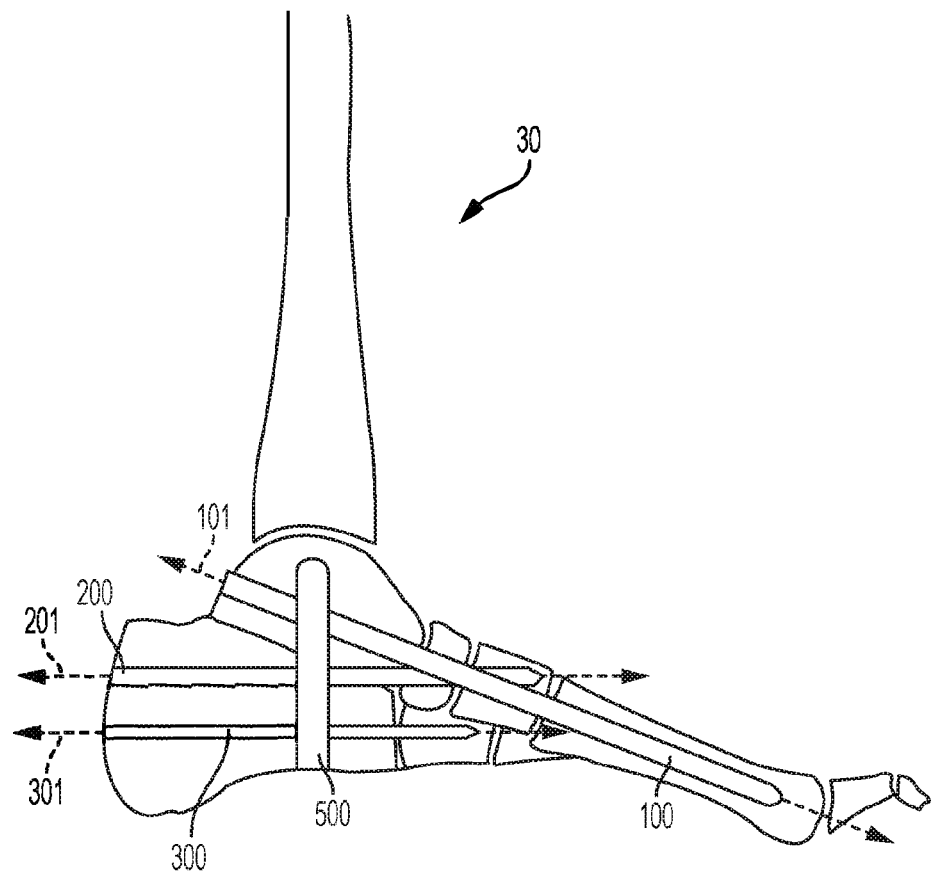
FIG. 5A illustrates a side schematic view of an embodiment of an internal ankle fixation system implanted in the foot in accordance with the present disclosure.
Figure 5B:
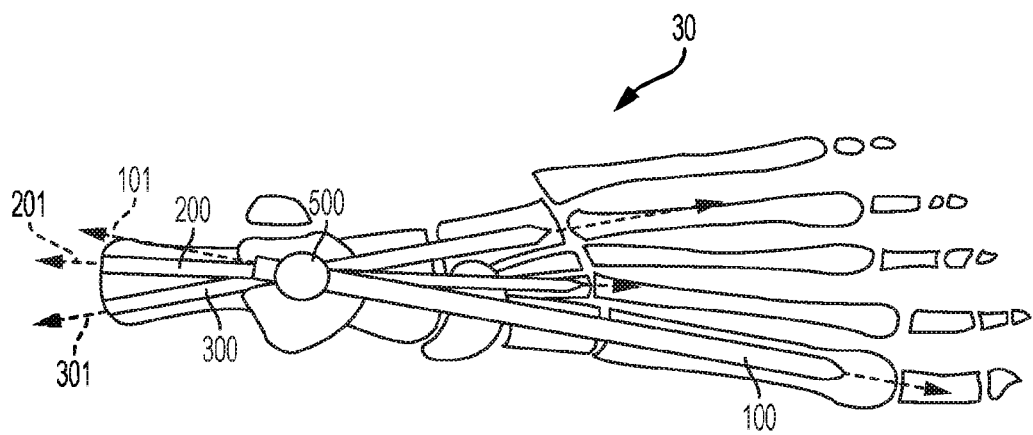
FIG. 5B illustrates a top schematic view of the embodiment shown in FIG. 5A.
Figure 6A:
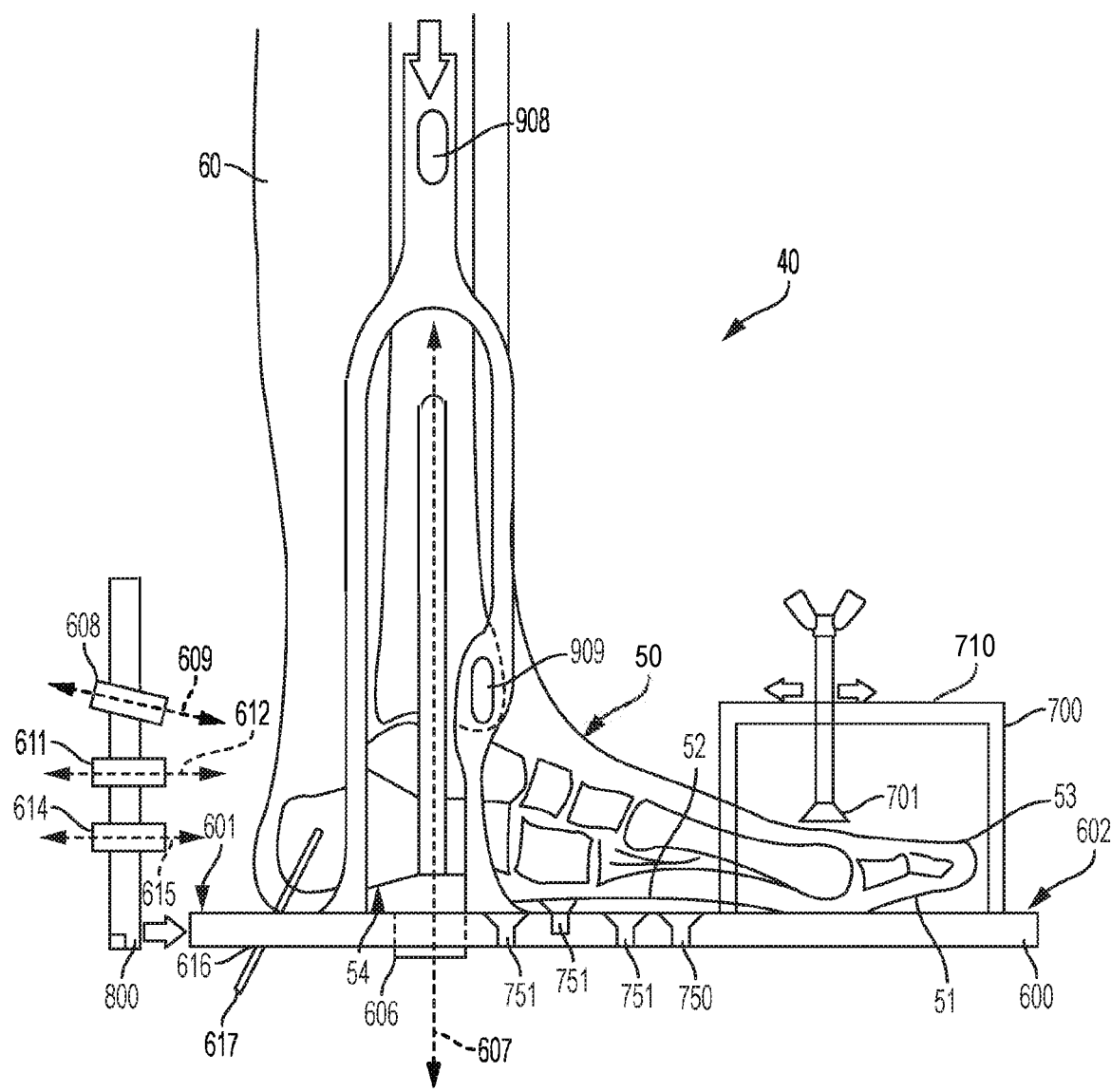
FIG. 6A illustrates a side schematic view of a foot securement and jig device in accordance with the present disclosure.
Figure 6B:
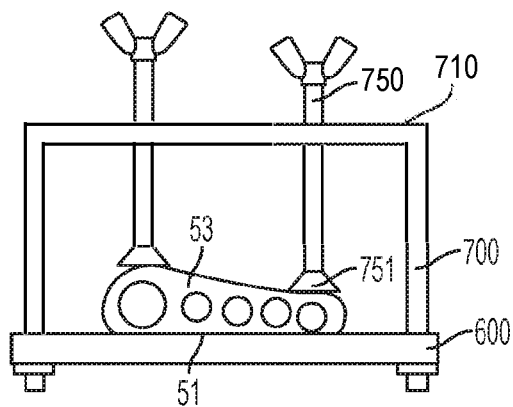
FIG. 6B illustrates a front schematic view of the foot securement and jig device shown in FIG. 6A.
Figure 6C:
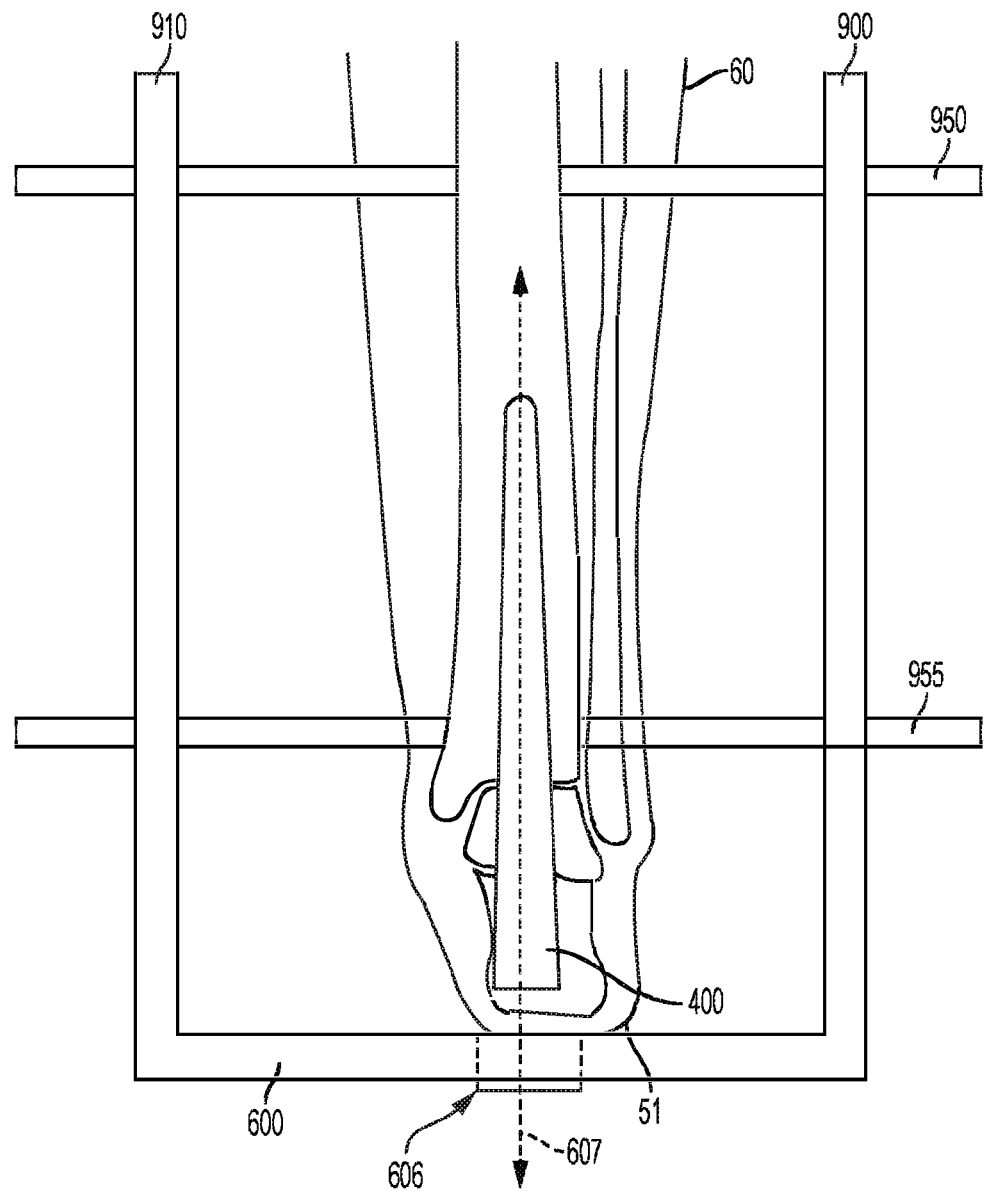
FIG. 6C illustrates a rear schematic view of the foot securement and jig device shown in FIG. 6A.
Figure 6D:
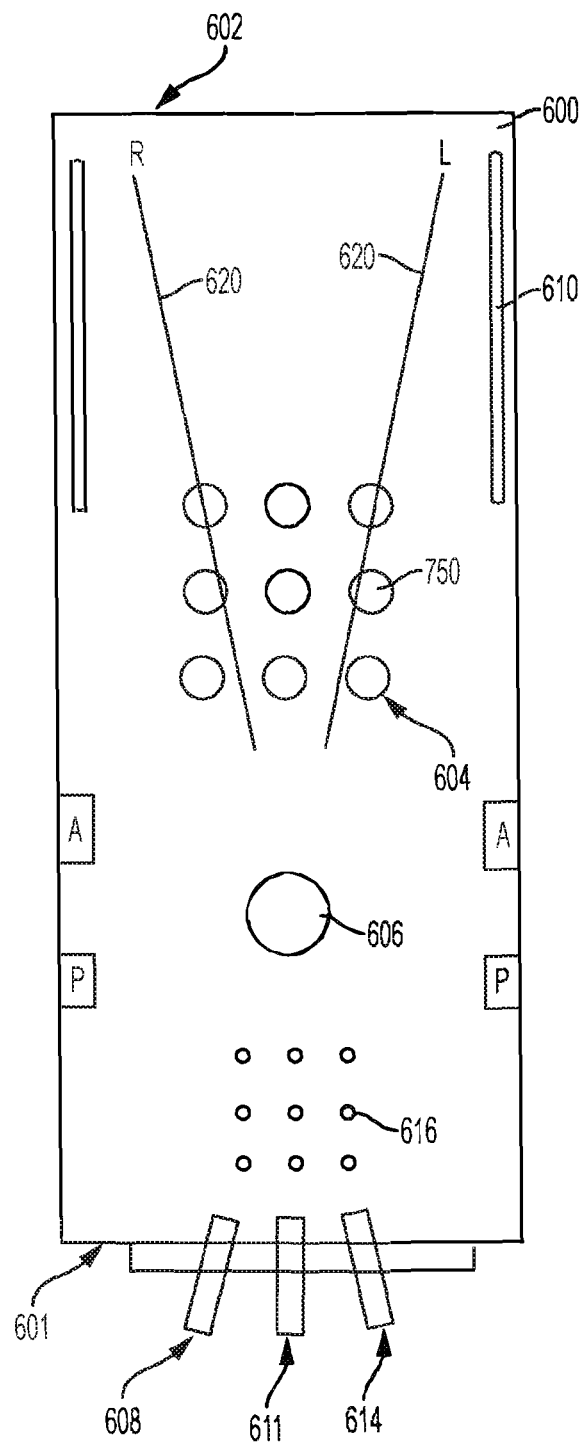
FIG. 6D illustrates a top schematic view of the foot supporting member, an element of the foot securement and jig device shown in FIG. 6A.

Alternatively, as shown in FIGS. 5A and 5B, an internal ankle fixation system 30 can comprise a fourth elongated fastener 500 that has a length sufficient to extend between and into a calcaneus and a talus, but not across the ankle joint into a tibia of a patient when implanted. Internal ankle fixation system 30 is essentially the same as system 10 shown in FIGS. 1A and 1B except that the fourth elongated fastener 500 is shorter and does not require slots or holes for facilitating securing to the tibia, as it does not extend into the tibia.

FIGS. 6A, 6B, 6C and 6D illustrate an embodiment of another aspect of the current disclosure, a foot securement and jig device 40 for the foot. Device 40 can comprise a foot supporting member configured to support a bottom surface 51 of a foot 50 (e.g., plate 600) with a proximal end 601 and a distal end 602. In order to facilitate shaping the longitudinal arch 52 and/or securing foot 50 to the foot supporting member, device 40 comprises a first press 700, configured to apply pressure to an upper surface 53 of the foot that is directed toward the foot supporting member and a second press 750, configured to apply pressure to the bottom surface (e.g., in the vicinity of the longitudinal arch 52) of the foot 50 that is directed away from the foot supporting member, when the bottom surface of the foot is supported by the foot supporting member. In the embodiment shown, plate 600 comprises at least one hole, slot or other opening 604 configured such that a portion of the second press 750 can extend there through.

Each press comprises members 701, 751, configured for contacting and applying pressure to the foot (e.g., a padded member). Foot contacting member 751 of second press 750 is spaced apart from the foot contacting member 701 of the first press 700 to facilitate shaping the longitudinal arch 52. The foot contacting member 701 of first press 700 is nearer the distal end than foot contacting member 751 of second press 750.

In the embodiment shown, first press 700 comprises a rigid support 710 that is configured to couple in fixed relation to plate 600 and configured to support one or more members 701. Each member 701 is configured to couple with rigid support 710 such that it can move away and towards plate 600, as selected by a clinician, but not from pressure applied by the foot. For example, member 701 can be threadably coupled to rigid support 710 such that rotation of member 701 causes movement towards or away from plate 600.

Rigid support 710 can be configured so that the location of the rigid support 710 relative to the foot supporting member is adjustable. For example, in the embodiment shown, plate 600 comprises one or more slots 610 and rigid support 710 is configured to slide within the slots at one time and couple in fixed relation to plate 600 at another time.

Each of the members 751 of second press 750 can be configured to couple with the foot supporting member (shown as plate 600) such that the members 751 can move away and towards the foot supporting member, as selected by a clinician, but not from pressure applied by foot 50. For example, member 751 can be threadably coupled to plate 600 such that rotation of member 751 causes movement towards or away from plate 600.

In some embodiments, each foot contacting member 701, 751 of each press 700, 750 can be configured such that the selective movement of each member relative to the plate is independent of the other members 701, 751 (if more than one) of that press 700, 750. Second press 750 in particular can comprise a plurality of members 751 located in close proximity to each other underneath the area of the longitudinal arch 52. Second press 750 can comprise at least 5, 10, 15 or more foot contacting members 751 that can be variably adjusted to define a desired contour of the longitudinal arch 52. The members 751 can define a contour that mimics the contour of the longitudinal arch 52 when under the load of walking or standing.

Foot supporting member, such as plate 600, can function as a jig to guide an elongated fastener (e.g., fourth elongated fastener 400 or 500 as described above) into the calcaneus and talus. For example, in the embodiment shown, plate 600 comprises a hole 606 that is configured to receive an elongated fastener (e.g., fourth elongated fastener 400 or 500, as described above) along an axis 607. Hole 606 is located between proximal end 601 and second press 750. When a foot is properly positioned on plate 600, the hindfoot 54 is disposed above hole 606 and the longitudinal arch 52 is positioned above hole 604 or second press 750. When a foot 50 is properly positioned on plate 600, axis 607 intersects with the calcaneus and talus or with the calcaneus, talus and tibia.

To facilitate fixing the position of the foot relative to the foot supporting member, the foot supporting member can comprise one or more holes 616 located between the proximal end 601 and second press 750 and configured so that an elongated fastener (such as pin 617) can be inserted into the calcaneus of foot 50. Plate 600 is shown comprising a plurality of holes 616. The selection of which to use or how many can depend on the foot. Once procedure is completed, pin 617 is removed.

The foot supporting member, such as plate 600, can also comprise at least one alignment marking 620, configured to inform proper alignment of the foot 50 on the foot supporting member and/or proper alignment on the foot supporting member relative to the jig 800 described below. Alignment marking 620 can be linear and define a line that intersects or bisects hole 606. The line can also be coplanar with axis 609 of jig 800 (described below). The foot would be placed on the foot supporting member and aligned with marking 620 so that the first metatarsal of the foot would intersect with axis 609.

Foot securement and jig device 40 can also comprise jig 800, configured to couple in fixed relation to the foot supporting member, e.g., at proximal end 601 of plate 600. Jig 800 comprises a plurality of holes to serve as guides. The plurality of holes of jig 800 are configured to receive an elongated fastener and guide the elongated fastener (e.g., first, second or third elongated fasteners 100, 200, 300, described above) along a desired axis. For example, hole 608 can be configured to receive an elongated fastener (e.g., first elongated fastener 100, described above) along axis 609. Jig 800 can also comprise hole 612 can be configured to receive another elongated fastener (e.g., second elongated fastener 200, described above) along an axis 612. Jig 800 can also comprise hole 614 configured to receive an elongated fastener (e.g., third elongated fastener 200, described above) along an axis 615. When foot 50 is in proper alignment within device 40, axis 609 can intersect with the talus and first metatarsal of foot 50, axis 612 can intersect with the calcaneus and the second cuneiform of foot 50 and/or axis 615 can intersect with the calcaneus and the cuboid of foot 50.

In addition, axis 607 and axis 612 are perpendicular, and axis 607 and axis 609 are oblique. Axis 607 and axis 615 are perpendicular. Axis 615 and axis 612 are skew. Hole 614 is located between the proximal end 601 of the plate 600 and hole 608. Hole 611 is located between the proximal end 601 of the plate 600 and hole 608.

Foot securement and jig device 40 can also comprise two lower leg supporting members 900, 910 configured such that a lower leg 60 is flanked by the two members 900, 910 when a bottom surface of the foot 50 is in contact with the plate 600 or other foot supporting member. Lower leg supporting members 900, 910 are configured to couple in fixed relation to the foot supporting member, e.g., plate 600.

Each lower leg supporting member 900, 910 is configured to couple with a length adjustable pin 950 such that the length adjustable pin will span the distance between the two lower leg support members 900, 910. For example, in the embodiment shown, each lower leg support member 900, 910 comprises a first slot 908 oriented to extend lengthwise along the lower leg support member 900, 910 and configured to receive the length adjustable pin 950 and permit sliding of the length adjustable pin 950 along the length of the first slot 908.

In addition, each lower leg support member 900, 910 can be configured to couple with a fixed length pin such that the fixed length pin will span the distance between the two lower leg support members 900, 910. For example, in the embodiment shown, each lower leg support member 900, 910 comprises a second slot 909 oriented to extend lengthwise along the lower leg support member 900, 910 and configured to receive the fixed length pin 955 and permit sliding of the fixed length pin 955 along the length of the second slot. Second slot 909 is located between the plate 600 and first slot 908. Pins 950 and 955 facilitate positioning and/or securing the tibia to the device 40.

Other embodiments of the present disclosure include methods for shaping a deformed foot using the jig system described above and methods for implanting an internal ankle fixation system into a patient, which can be done after the foot is secured to the jig system.

In an embodiment, a method of implanting an internal ankle fixation system into a patient or reconstructing the foot can comprise inserting the fourth elongated member into a calcaneus, talus, and optionally a tibia of the patient and inserting a first, second, or third elongated member into a talus and at least one of a cuboid, a cuneiform, or a first metatarsal of the patient, whereby the fourth elongated member intersects with the first, second, or third elongated member. In some embodiments, the first elongated member is inserted into talus and the first metatarsal of the patient, the second elongated member is inserted into talus and the cuboid of the patient, and the third elongated member is inserted into talus and the cuneiform of a patient.

Prior to implanting the elongated members, the foot is secured to a jig system as described above. In some embodiments, securing a foot of the patient to a jig system comprises passing a pin through the plate and into the calcaneus of the patient.

In some embodiments, a method of shaping or reshaping the foot can comprise securing a foot of the patient to the jig system and applying pressure to the foot with the first press, the second press, or both. The pressure is sufficient, for example, to shift the positions of the bones within the midfoot and/or forefoot In some embodiments, a method of shaping or reshaping the foot can comprise securing a foot of the patient to the jig system and applying pressure to the foot with the first press, the second press, or both. The pressure is sufficient, for example, to shift the positions of the bones within the midfoot and/or forefoot Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. An internal fixation ankle support system comprising:
a first elongated fastener configured to be inserted into bone and having a length that is sufficient to extend between and into a talus and a metatarsal of a patient when implanted;
a second elongated fastener configured to be inserted into bone and having a length that is sufficient to extend into a calcaneus, a talus, and optionally a tibia of a patient when implanted; and
a third elongated fastener configured to be inserted into bone and having a length that is sufficient to extend between and into a talus and at least one of a cuboid or a cuneiform of a patient when implanted, wherein the second elongated fastener comprises a first hole configured to receive the first elongated fastener along a first axis, whereby the first elongated fastener extending through the first hole is intersecting the second elongated fastener, wherein the second elongated fastener comprises a second hole configured to receive the third elongated fastener along a second axis, whereby the third elongated fastener extending through the second hole is intersecting the second elongated fastener, and wherein one or more of the first elongated fastener member and third elongated fastener member is configured for polyaxial coupling and locking in relation to the second elongated fastener.

2. The internal fixation ankle support system of claim 1 further comprising:

a fourth elongated fastener configured to be inserted into bone and having a length that is sufficient to extend between and into a talus and at least one of a cuboid or a cuneiform of a patient when implanted;

wherein the second elongated fastener comprises a third hole configured to receive the fourth elongated fastener along a third axis, whereby the fourth elongated fastener extending through the third hole is intersecting the second elongated fastener.

3. The internal fixation ankle support system of claim 2, wherein the first or third elongated fastener comprises an outer elongated body comprising a longitudinal bore and an elongated reinforcing member configured to be inserted into the longitudinal bore.

4. The internal fixation ankle support system of claim 3, wherein the reinforcing member is composed of a material that has a higher elastic modulus than the outer elongated body.

5. The internal fixation ankle support system of claim 2, wherein the second elongated fastener is longer than the first elongated fastener.

6. The internal fixation ankle support system of claim 5, wherein the first elongated fastener is at least 1.5 times the length of the third elongated fastener or fourth elongated fastener and wherein the second elongated fastener is longer than the third elongated fastener or fourth elongated fastener.

7. The internal fixation ankle support system of claim 6, wherein a transverse dimension of the second elongated fastener is greater than a transverse dimension of the first, third and fourth elongated fasteners, individually.

8. The internal fixation ankle support system of claim 7, wherein a transverse dimension of the first elongated fastener is greater than a transverse dimension of the third elongated fastener or fourth elongated fastener.

9. The internal fixation ankle support system of claim 2, wherein one or more of the second axis and the third axis is perpendicular or oblique relative to the longitudinal axis of the second elongated fastener.

10. The internal fixation ankle support system of claim 9, further comprising one or more of: the first axis being skew relative to the second axis, the first axis being skew relative to the third axis, or the second axis being skew relative to the third axis.

11. The internal fixation ankle support system of claim 2, wherein the second hole and the third hole are located between the second end of the second elongated fastener and the first hole.

12. The internal fixation ankle support system of claim 11, wherein the second elongated fastener further comprises a fourth hole that is located between the first end and the first hole.

13. The internal fixation ankle support system of claim 12, wherein the second elongated fastener further comprises a first slot that is located between the fourth hole and the first hole.

14. The internal fixation ankle support system of claim 13, wherein the second elongated fastener further comprises a second slot that is located between the first slot and the first hole.

15. The internal fixation ankle support system of claim 2, wherein the second elongate fastener comprises a longitudinal bore having an internal thread and being accessible at the second end and a compression screw configured to be inserted into the longitudinal bore to move the first, second, and third elongate fasteners in the direction of the longitudinal axis of the fourth elongate fastener.

16. The internal fixation ankle support system of claim 1, wherein the first axis and the longitudinal axis of the second elongated fastener are oblique.

17. The internal fixation ankle support system of claim 1, wherein the first end of the second elongated fastener is tapered.

18. An internal fixation ankle support system comprising:

a first elongated fastener configured to be inserted into bone and having a length that is sufficient to extend between and into a talus and a metatarsal of a patient when implanted;

a second elongated fastener configured to be inserted into bone and having a length that is sufficient to extend into a calcaneus, a talus, and optionally a tibia of a patient when implanted; and a third elongated fastener configured to be inserted into bone and having a length that is sufficient to extend between and into a talus and at least one of a cuboid or a cuneiform of a patient when implanted, wherein the second elongated fastener comprises a first hole configured to receive the first elongated fastener along a first axis, whereby the first elongated fastener extending through the first hole is intersecting the second elongated fastener, a fourth elongated fastener configured to be inserted into bone and having a length that is sufficient to extend between and into a talus and at least one of a cuboid or a cuneiform of a patient when implanted;

wherein the second elongated fastener comprises a third hole configured to receive the fourth elongated fastener along a third axis, whereby the fourth elongated fastener extending through the third hole is intersecting the second elongated fastener, wherein the second elongated fastener comprises a second hole configured to receive the third elongated fastener along a second axis, whereby the third elongated fastener extending through the second hole is intersecting the second elongated fastener, and wherein one or more of the first elongated fastener member, third elongated fastener member or fourth elongated fastener member is configured for polyaxial coupling to couple in fixed and fully-inserted relation to the second elongated fastener at an angle selected from a plurality of angles by a surgeon.

* * * * *